(12) United States Patent
Ibrahim et al.

(10) Patent No.: US 9,572,624 B2
(45) Date of Patent: Feb. 21, 2017

(54) BIPOLAR BELT SYSTEMS AND METHODS

(75) Inventors: Tamer Ibrahim, Pleasant Hill, CA (US); David K. Swanson, Campbell, CA (US)

(73) Assignee: Atricure, Inc., Mason, OH (US)

( * ) Notice: Subject to any disclaimer, the term of this patent is extended or adjusted under 35 U.S.C. 154(b) by 954 days.

(21) Appl. No.: 12/850,944

(22) Filed: Aug. 5, 2010

(65) Prior Publication Data

US 2011/0034915 A1 Feb. 10, 2011

Related U.S. Application Data

(60) Provisional application No. 61/231,613, filed on Aug. 5, 2009.

(51) Int. Cl.
| | | |
|---|---|---|
| *A61B 18/14* | (2006.01) | |
| *A61B 18/18* | (2006.01) | |
| *A61B 18/12* | (2006.01) | |
| *A61B 18/16* | (2006.01) | |
| *A61B 18/20* | (2006.01) | |
| *A61B 17/22* | (2006.01) | |
| *A61B 18/00* | (2006.01) | |

(52) U.S. Cl.
CPC ............ *A61B 18/18* (2013.01); *A61B 18/1206* (2013.01); *A61B 18/16* (2013.01); *A61B 18/20* (2013.01); *A61B 2017/22005* (2013.01); *A61B 2018/00375* (2013.01); *A61B 2018/00702* (2013.01); *A61B 2018/00791* (2013.01); *A61B 2018/1407* (2013.01)

(58) Field of Classification Search
CPC ....... A61B 18/04; A61B 18/08; A61B 18/082; A61B 18/10; A61B 18/12; A61B 18/1206; A61B 18/1266; A61B 18/14; A61B 18/1442; A61B 18/1445; A61B 18/1466; A61B 18/16; A61B 18/18; A61B 18/20; A61B 2018/00375; A61B 2018/00702; A61B 2018/00791; A61B 2018/1407; A61B 2017/22005
USPC .............................................. 606/33, 34, 41
See application file for complete search history.

(56) References Cited

U.S. PATENT DOCUMENTS

| 3,745,998 A | 7/1973 | Rose |
| 4,224,929 A | 9/1980 | Furihata |
| (Continued) | | |

OTHER PUBLICATIONS

Borst, Cornelius, et al., "Coronary artery bypass grafting without cardiopulmonary bypass and without interruption of native coronary flow using a novel anastomosis site restraining device ("Octopus")," JACC vol. 27, No. 6, May 1996, pp. 1356-1364.

(Continued)

*Primary Examiner* — Michael Peffley
*Assistant Examiner* — Khadijeh Vahdat
(74) *Attorney, Agent, or Firm* — Levine Bagade Han LLP

(57) ABSTRACT

Bipolar belt ablation systems and methods for treating patient tissue involve the use of an ablation an ablation apparatus with a plurality of ablation elements carried by a flexible tube structure, a radiofrequency generator capable of delivering a plurality of differing radiofrequency power signals to the ablation elements of the ablation device, wires transmitting the radiofrequency power signals from the radiofrequency generator to the ablation elements, and a control mechanism to enable temperature-based power control to each of the powered ablation elements.

31 Claims, 4 Drawing Sheets

(56) References Cited

U.S. PATENT DOCUMENTS

| | | | |
|---|---|---|---|
| 4,445,892 A | 5/1984 | Hussein et al. | |
| 4,961,738 A | 10/1990 | Mackin | |
| 4,991,578 A | 2/1991 | Cohen | |
| 5,336,252 A | 8/1994 | Cohen | |
| 5,409,483 A | 4/1995 | Campbell et al. | |
| 5,423,805 A | 6/1995 | Brucker et al. | |
| 5,503,617 A | 4/1996 | Jako | |
| 5,593,405 A | 1/1997 | Osypka | |
| 5,672,153 A | 9/1997 | Lax et al. | |
| 5,727,569 A | 3/1998 | Benetti et al. | |
| 5,782,746 A | 7/1998 | Wright | |
| 5,807,243 A | 9/1998 | Vierra et al. | |
| 5,836,311 A | 11/1998 | Borst et al. | |
| 5,865,730 A | 2/1999 | Fox et al. | |
| 5,927,284 A | 7/1999 | Borst et al. | |
| 5,976,132 A | 11/1999 | Morris | |
| 6,013,027 A | 1/2000 | Khan et al. | |
| 6,015,378 A | 1/2000 | Borst et al. | |
| 6,036,641 A | 3/2000 | Taylor et al. | |
| 6,036,685 A | 3/2000 | Mueller | |
| 6,039,733 A | 3/2000 | Buysse et al. | |
| 6,053,910 A * | 4/2000 | Fleenor | A61B 18/16 606/32 |
| 6,086,586 A | 7/2000 | Hooven | |
| 6,110,106 A | 8/2000 | MacKinnon et al. | |
| 6,161,543 A | 12/2000 | Cox et al. | |
| 6,237,605 B1 | 5/2001 | Vaska et al. | |
| 6,251,065 B1 | 6/2001 | Kochamba et al. | |
| 6,277,065 B1 | 8/2001 | Donofrio | |
| 6,309,349 B1 | 10/2001 | Bertolero et al. | |
| 6,328,688 B1 | 12/2001 | Borst et al. | |
| 6,334,843 B1 | 1/2002 | Borst et al. | |
| 6,336,898 B1 | 1/2002 | Borst et al. | |
| 6,338,712 B2 | 1/2002 | Spence et al. | |
| 6,338,738 B1 | 1/2002 | Bellotti et al. | |
| 6,346,077 B1 | 2/2002 | Taylor et al. | |
| 6,350,229 B1 | 2/2002 | Borst et al. | |
| 6,352,534 B1 | 3/2002 | Paddock et al. | |
| 6,364,826 B1 | 4/2002 | Borst et al. | |
| 6,371,906 B1 | 4/2002 | Borst et al. | |
| 6,390,976 B1 | 5/2002 | Spence et al. | |
| 6,394,948 B1 | 5/2002 | Borst et al. | |
| 6,463,332 B1 | 10/2002 | Aldrich | |
| 6,464,630 B1 | 10/2002 | Borst et al. | |
| 6,482,151 B1 | 11/2002 | Vierra et al. | |
| 6,484,727 B1 | 11/2002 | Vaska et al. | |
| 6,511,416 B1 | 1/2003 | Green, II et al. | |
| 6,514,250 B1 | 2/2003 | Jahns et al. | |
| 6,522,905 B2 | 2/2003 | Desai | |
| 6,524,338 B1 | 2/2003 | Gundry | |
| 6,527,767 B2 | 3/2003 | Wang et al. | |
| 6,544,263 B2 | 4/2003 | Morgan et al. | |
| 6,595,989 B1 | 7/2003 | Schaer | |
| 6,599,237 B1 | 7/2003 | Singh | |
| 6,645,202 B1 | 11/2003 | Pless et al. | |
| 6,652,518 B2 | 11/2003 | Wellman et al. | |
| 6,758,809 B2 | 7/2004 | Briscoe et al. | |
| 6,849,075 B2 | 2/2005 | Bertolero et al. | |
| 6,890,295 B2 | 5/2005 | Michels et al. | |
| 7,018,328 B2 | 3/2006 | Mager et al. | |
| 7,226,448 B2 | 6/2007 | Bertolero et al. | |
| 7,237,555 B2 | 7/2007 | Kochamba et al. | |
| 7,338,434 B1 | 3/2008 | Haarstad et al. | |
| 7,542,807 B2 | 6/2009 | Bertolero et al. | |
| 7,594,915 B2 | 9/2009 | Kochamba et al. | |
| 7,682,305 B2 | 3/2010 | Bertolero et al. | |
| 7,749,157 B2 | 7/2010 | Bertolero | |
| 7,819,867 B2 | 10/2010 | Bertolero et al. | |
| 2002/0026094 A1 | 2/2002 | Roth | |
| 2002/0056460 A1 | 5/2002 | Boyd | |
| 2002/0068855 A1 | 6/2002 | Daniel et al. | |
| 2002/0099270 A1 | 7/2002 | Taylor et al. | |
| 2002/0099390 A1 | 7/2002 | Kaplan | |
| 2002/0161361 A1 * | 10/2002 | Sherman | A61B 18/1206 606/34 |
| 2002/0177846 A1 | 11/2002 | Mulier et al. | |
| 2003/0009080 A1 | 1/2003 | Peng et al. | |
| 2003/0010346 A1 | 1/2003 | Paolitto et al. | |
| 2003/0060685 A1 | 3/2003 | Houser et al. | |
| 2003/0158463 A1 | 8/2003 | Julian et al. | |
| 2003/0158464 A1 | 8/2003 | Bertolero | |
| 2003/0199862 A1* | 10/2003 | Simpson et al. | 606/34 |
| 2004/0049182 A1* | 3/2004 | Koblish et al. | 606/41 |
| 2005/0010179 A1 | 1/2005 | Bertolero et al. | |
| 2005/0119653 A1 | 6/2005 | Swanson | |
| 2005/0119654 A1 | 6/2005 | Swanson et al. | |
| 2005/0240175 A1 | 10/2005 | Bertolero et al. | |
| 2006/0015165 A1 | 1/2006 | Bertolero et al. | |
| 2006/0155272 A1 | 7/2006 | Swanson | |
| 2007/0233226 A1 | 10/2007 | Kochamba et al. | |
| 2008/0294154 A1 * | 11/2008 | Ibrahim | A61B 18/1492 606/13 |
| 2009/0048591 A1 | 2/2009 | Ibrahim et al. | |
| 2009/0076501 A1 | 3/2009 | Bertolero et al. | |
| 2009/0076537 A1 | 3/2009 | Bertolero | |
| 2009/0163768 A1 | 6/2009 | Ibrahim et al. | |
| 2009/0281541 A1 | 11/2009 | Ibrahim et al. | |
| 2010/0036195 A1 | 2/2010 | Bertolero et al. | |

OTHER PUBLICATIONS

Jansen, Erik, et al., "Less Invasive off-pump CABG using a suction device for immobilization: The Octopus method," European Journal of Cardiothoracic surgery 12 (1997) pp. 406-412.

* cited by examiner

BIPOLAR BELT SYSTEMS AND METHODS

CROSS-REFERENCES TO RELATED APPLICATIONS

This application is a nonprovisional of, and claims the benefit of the filing date of, U.S. Provisional Patent Application No. 61/231,613, filed Aug. 5, 2009, the entire disclosure of which is incorporated herein by reference for all purposes.

BACKGROUND OF THE INVENTION

Embodiments of the present invention relate in general to systems and methods for ablating tissue, and in particular instances to bipolar belt ablation systems and methods.

Several types of unipolar wand or belt type devices have been described. A suction applied bipolar ablation device with two adjacent ablation elements to produce an arcing energy delivery pattern has been described.

Although these and other proposed treatments may provide real benefits to patients in need thereof, still further advances would be desirable. Embodiments of the present invention provide solutions that address the problems which may be associated with the techniques described above, and hence provide answers to at least some of these outstanding needs.

BRIEF SUMMARY OF THE INVENTION

Embodiments of the present invention provide systems and methods for encircling tissue structures such as pulmonary veins, and applying ablative energy thereto. Systems for ablating tissue can be used with any preferred surgical access technique, including without limitation sternotomy and thoracotomy procedures.

In one aspect, embodiments of the present invention encompass radiofrequency ablation systems for treating tissue. Exemplary systems may include an ablation apparatus with a plurality of ablation elements carried by a flexible tube structure, and a radiofrequency generator capable of delivering a plurality of differing radiofrequency power signals to the ablation elements of the ablation device. Systems may also include transmission elements such as wires that transmit the radiofrequency power signals from the radiofrequency generator to the ablation elements, and a control mechanism to enable temperature-based power control to each of the powered ablation elements. In some cases, the plurality of power signals include the output of the radiofrequency generator and the return path of the generator. In some cases, the plurality of power signals include at least two separate outputs of the radiofrequency generator. Optionally, at least two separate outputs of the radiofrequency generator can have the same frequency but differ in at least one of amplitude or phase from other power outputs. According to some embodiments, two separate outputs of the radiofrequency generator can have different frequencies. In some cases, one or more electrode pads placed on the skin of the patient can provide a return path to the generator. In some cases, one or more electrodes on the ablation apparatus may provide the only return path to the generator. Optionally, the ablation apparatus can be configured to enable placement of the ablation elements on the epicardium of the heart. Exemplary embodiments also encompass a radiofrequency ablation apparatus that enables placement of the ablation elements near the pulmonary veins. In some cases, the ablation apparatus can be adapted to enable ablation of atrial tissue at least partially encircling the pulmonary veins. Optionally, an ablation apparatus can be adapted to enable ablation of atrial tissue to isolate tissue activation within at least one pulmonary vein from the rest of the atrium. In some instances, operation of an ablation apparatus provides a contiguous lesion around all pulmonary veins without needing to move the ablation elements during the lesion-making process. According to exemplary embodiments, the ablation apparatus may form a loop with more proximal ablation elements in close proximity to one or more distal ablation elements. In some cases, the ablation apparatus may provide a contiguous lesion around all pulmonary veins without needing to move the ablation elements during the lesion-making process. Optionally, a loop can be formed using a cinching structure or mechanism. In some cases, a cinching structure uses one or more magnets to form the loop. Optionally, the cinching structure may use the interference fit of a snap connection to form the loop. In some cases, the cinching structure uses suction to form the loop. In some instances, the ablation apparatus includes one or more suction pods to enhance tissue contact to the ablation elements.

In another aspect, embodiments of the present invention encompass methods of administering a radiofrequency ablation treatment to a patient. Exemplary methods include delivering a plurality of differing radiofrequency power signals to a plurality of ablation elements of an ablation apparatus. The plurality of ablation elements can be coupled with a flexible tube structure. Methods may also include sensing a temperature of a tissue of the patient, and controlling power to one or more of the ablation elements based on the sensed temperature. Optionally, methods may include using an introducer during the course of the treatment. In some cases, methods involve using an endoscopic visualization apparatus during the course of the treatment.

In a further aspect, embodiments of the present invention encompass a radiofrequency ablation system for treating tissue. The system can include an ablation apparatus having a first ablation element and a second ablation element carried by a flexible tube structure. The system can also include a radiofrequency generator capable of generating a first radiofrequency power signal for the first ablation element and a second radiofrequency power signal for the second ablation element. Exemplary systems also include a first transmission element configured to transmit the first radiofrequency power signal from the radiofrequency generator to the first ablation element and a second transmission element configured to transmit the second radiofrequency power signal from the radiofrequency generator to the second ablation element. Some systems may include a control mechanism to enable temperature-based power control to each of the powered ablation elements. In some instances, the first radiofrequency power signal is equivalent to the second radiofrequency power signal. In some instances, the first radiofrequency power signal is different from the second radiofrequency power signal.

In yet another aspect, embodiments of the present invention encompass methods of administering a radiofrequency ablation treatment to a patient. Exemplary methods may include delivering a first radiofrequency power signal to a first ablation element of an ablation apparatus and delivering a second radiofrequency power signal to a second ablation element of the ablation apparatus. Optionally, methods may include sensing a temperature of a tissue of the patient, and controlling power to at least one of the first ablation element or the second ablation element based on the sensed temperature. According to some methods, the first radiofrequency power signal is equivalent to the second radiofrequency power signal. In some instances, the first radiofrequency power signal is different from the second radiofrequency power signal.

For a fuller understanding of the nature and advantages of the present invention, reference should be had to the ensuing detailed description taken in conjunction with the accompanying drawings.

DETAILED DESCRIPTION OF THE INVENTION

Figure 1:
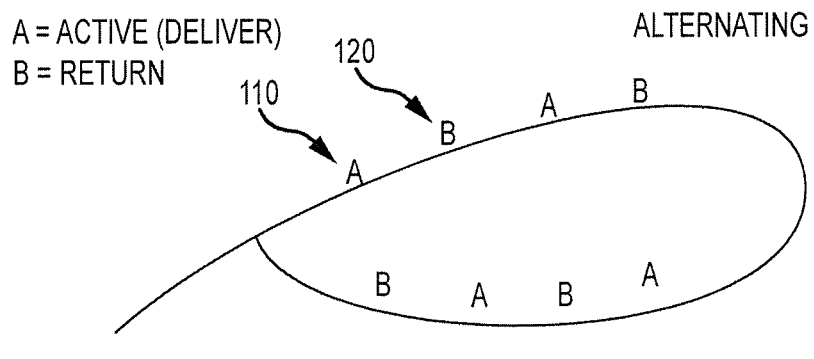
FIG. 1 illustrates aspects of tissue treatment system according to embodiments of the present invention.
Figure 2:
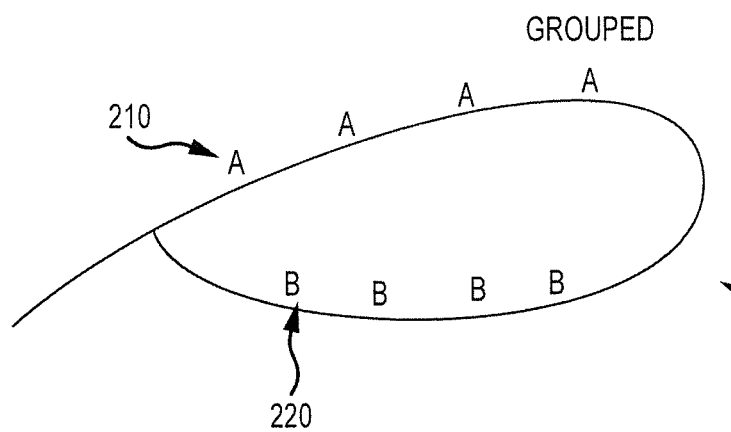
FIG. 2 illustrates aspects of tissue treatment system according to embodiments of the present invention.
Figure 3:
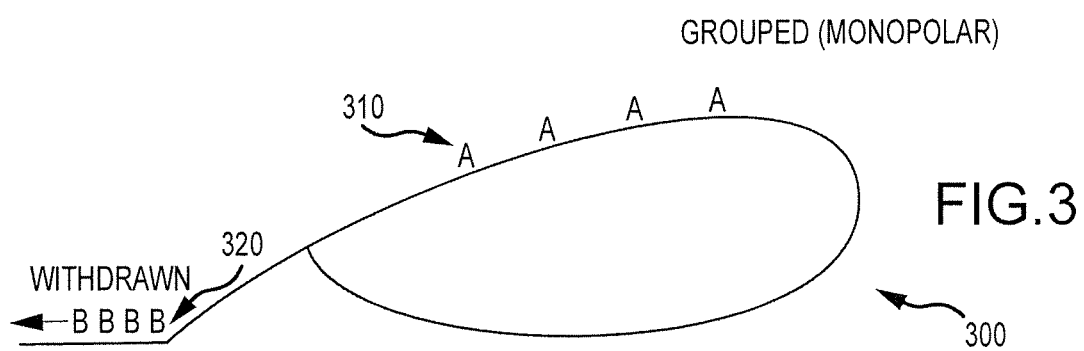
FIG. 3 illustrates aspects of tissue treatment system according to embodiments of the present invention.

Embodiments of the present invention encompass multi-element belt type ablation devices for encircling tissue structures such as one or more pulmonary veins. Ablation elements can deliver RF energy and can be configured such that certain elements deliver the RF and other elements provide the return path. Various configurations are possible and two particular embodiments are described including alternating and grouped opposing. For example, FIG. 1 illustrates an embodiment of a treatment system 100 which is configured to deliver an alternating treatment protocol. Treatment system 100 includes active or delivery electrodes 110 and return electrodes 120. FIG. 2 shows a treatment system 200 which is configured to deliver a grouped or opposing treatment protocol. Treatment system 200 includes active or delivery electrodes 210 and return electrodes 220. As shown in FIG. 3, a treatment system 300 which is configured to deliver a grouped or opposing treatment protocol can also be used as a monopolar ablation device to deliver a monopolar ablation. As depicted here, treatment system 300 includes active or delivery electrodes 310, and return path electrodes 320 which have been withdrawn.

According to some embodiments, devices may include a cinching mechanism to allow a circumference to be adjustable to the tissue structure to be ablated, and also to allow the active and return path electrodes on opposing sides of a tissue structure to be brought into closer proximity to one another. A cinching mechanism may be facilitated or constructed by fixing the distal end of the belt and retracting the proximal end or by a separate mechanism that cinches both distal and proximal ends.

Figure 4A:
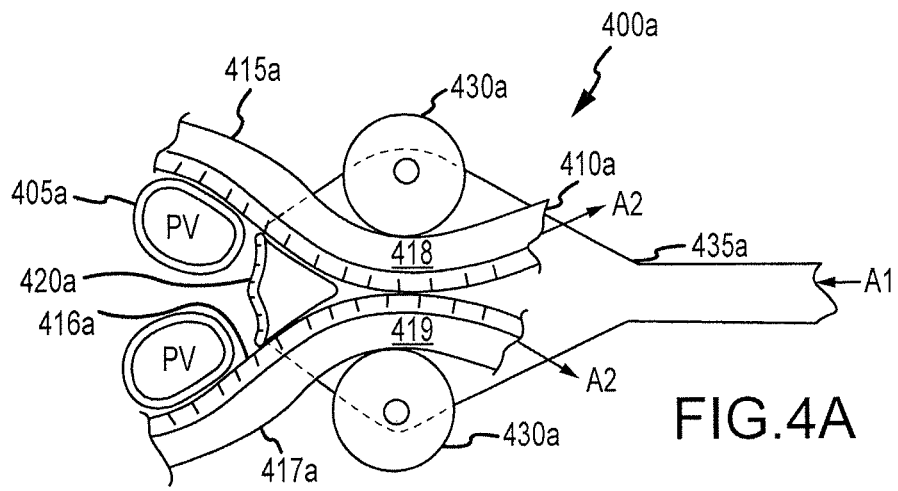
FIGS. 4A, 4B, and 4C illustrates aspects of tissue treatment system according to embodiments of the present invention.
Figure 4B:
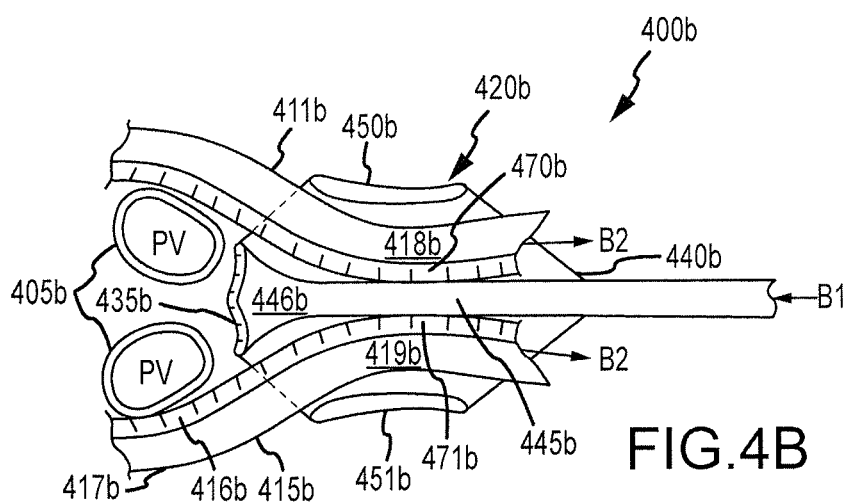
Figure 4C:
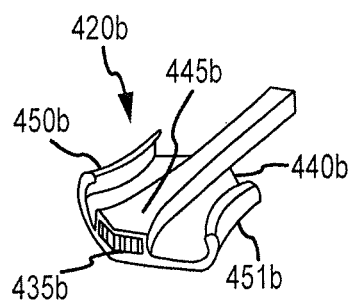

FIGS. 4A-4C show aspects of ablation systems according to embodiments of the present invention. An ablation system 400a is depicted in FIG. 4A. Ablation system 400a includes an ablation assembly 415a and a cinching device 410a. Ablation assembly 415a includes an ablation member 416a and a stabilizer member 417a. Cinching device 410a includes or is coupled with an ablation segment 420a such as a corner electrode. Cinching device 410a includes a support 435a and one or more rollers 430a. Ablation segment 420a can be coupled with support 435a as part of cinching device 410a. Ablation segment 420a may be positioned on support 435a toward a distal end of cinching device 410a, so that when an operator or surgeon advances cinching device 410a towards pulmonary veins (PV) of patient tissue 405a, ablation segment 420a can make contact with the atria adjacent to the pulmonary veins. In some embodiments, ablation segment 420a can be used to help insure or increase the likelihood that the ablation system ablates the patient tissue 405a in an approximate or complete circle or closed path around the patient tissue. Ablation segment 420a can be designed to bridge the gap between opposing sides of ablation element 416a, so that a loop structure is formed in more of a smooth circumferential path and in less of a teardrop shaped path. Ablation segment 420a can thus be used to bridge a gap that might otherwise exist between ablation member 415a and patient tissue 405a. In some embodiments, ablation member 416a may be coupled with ablation segment 420a. In some embodiments, the ablation segment or member may include a material that is capable of transmitting different forms of energy, including but not limited to RF, thermoelectric, cryogenic, microwave, laser, ultrasound, or the like. In some embodiments, ablation segment 420a can be positioned in order to inhibit the ablation assembly 415a from pinching the patient tissue 405a. Ablation member 416a may include active and return delivery electrode configurations as discussed elsewhere herein, for example with reference to FIGS. 1 to 3.

In some embodiments, the ablation segment 420a may be shaped in order to maximize contact with the patient tissue 405a. In some embodiments, the ablation segment 420a may be shaped in order to minimize or reduce any pinching of the patient tissue 405a. Ablation segment 420a may be rigid in some embodiments. Ablation segment 420a may be flexible in some embodiments. Ablation segment 420a may make contact with the ablation member 416a. Optionally, ablation segment 420a may not make contact with the ablation member 416a. Cinching device 410a can be advanced in a direction toward the patient tissue 405a as indicated by arrow A1, to increase the amount of contact between ablation member 417a and the patient tissue 405a or to help secure the position of ablation member 417a relative to patient tissue 405a. Similarly, by advancing cinching device 410a in this direction, an operator can increase the amount of contact between ablation segment 420a and the patient tissue 405a or help secure the position of ablation segment 420a relative to patient tissue 405a. The operator can also establish or apply an opposing force by grasping or pulling sections 418a, 419a of ablation assembly 415a in an opposing direction, as indicated by arrows A2. The operator can position ablation assembly 415a to make contact with selected parts of patient tissue 405a such that when ablative energy is transmitted through the ablation assembly, it is possible to create an approximately circular or closed ablation pattern or lesion on the tissue. In this way, energy can be applied by the ablation system to the tissue. The position of cinching device 410a relative to ablation assembly 415a can be adjusted by the operator. For example, the cinching device may be advanced or retracted to differing degrees in order to increase or decrease an amount of contact between the ablation assembly and the patient tissue. Ablation segment 420a in combination with ablation member 416a can form a continuous circumferential loop that can be used to ablate a circumferential lesion on the patient tissue.

As shown in FIGS. 4B and 4C, an ablation system 400b can include a cinching device 420b and an ablation assembly 415b. Cinching device 420b can include one or more guides 450b, and can be used in operative association with an ablation assembly 415b having an ablation member 416b and a stabilizer member 417b. Cinching device 420b can also include an ablation member protection mechanism 445b which can be disposed between portions 470b and 471b of ablation member 416b. Hence, it is possible to avoid contact between different portions of an ablation member such as an electrode. One or more guides 450b, 451b of cinching device 420b may include a flat or curved retaining wall perpendicularly attached to, or formed along with, a support 440b of cinching device 420b. In some embodiments, one or more guides 450b, 451b may have a curved top edge. The shape of guides 450b, 451b can be designed in order to help facilitate positioning an ablation assembly 415b around the patient tissue 405b by keeping distal 471b and proximal 470b segments of the ablation member 416b close to each other. In an embodiment with two or more guides, the guides may be located on opposite sides of a support plate of cinching device 420b. In one method for using the cinching device 420b with guides, ablation assembly 415b can be passed through the cinching device along one guide 450b and then wrapped around the patient tissue 405b. The ablation assembly 415b can then be pulled through cinching device 420b in the opposed direction, passing along another guide 451b. The guides may be made of or include various semi-rigid or rigid materials. Cinching device 420b can be advanced in a direction toward the patient tissue 405b as indicated by arrow B1, to increase the amount of contact between the ablation member 417b and the patient tissue 405b or to help secure the position of ablation member 417b relative to patient tissue 405b. Similarly, by advancing cinching device 420b in this direction, an operator can increase the amount of contact between ablation segment 435b and the patient tissue 405b or help secure the position of ablation segment 435b relative to patient tissue 405b. The operator can also establish or apply an opposing force by grasping or pulling sections 418b, 419b of ablation assembly 415b in an opposing direction, as indicated by arrows B2.

In some embodiments, as cinching device 420b is advanced towards the patient tissue 405b, a loop structure 411b of the ablation assembly 415b is reduced in diameter or otherwise contracted. As shown in FIG. 4B, in some embodiments, an ablation member protection mechanism 445b can be utilized along with the cinching device 420b. Cinching device 420b can include ablation member protection mechanism 445b disposed between guides 450b, 451b. Ablation member protection mechanism 445b can act to keep a first segment 470a and a second segment 471b of the ablation member from making contact with each other. Ablation member protection mechanism 445b may either be fixed or integral to cinching device 420b or separate from cinching device 420b. In some embodiments, an ablation segment 435b may be attached with cinching device 420b, such as with a first or distal section 446b of ablation member protection mechanism 445b. Ablation segment 435b can be utilized to increase the amount of contact between the ablation assembly 415b and the patient tissue 405b. Ablation segment 435b can also be utilized to reduce pinching of the patient tissue 405b that might otherwise occur if ablation segment 435b were not disposed between opposing segments of ablation member 416b. The operator can position ablation assembly 415b to make contact with selected parts of patient tissue 405b such that when ablative energy is transmitted through the ablation assembly, it is possible to create an approximately circular or closed ablation pattern or lesion on the tissue. In this way, energy can be applied by the ablation system to the tissue. The position of cinching device 420b relative to ablation assembly 415b can be adjusted by the operator. For example, the cinching device may be advanced or retracted to differing degrees in order to increase or decrease an amount of contact between the ablation assembly and the patient tissue. Ablation segment 435b in combination with ablation member 416b can form a continuous circumferential loop that can be used to ablate a circumferential lesion on the patient tissue. Ablation member 416b may include active and return delivery electrode configurations as discussed elsewhere herein, for example with reference to FIGS. 1 to 3. FIG. 4C shows a perspective view of cinching device 420b which includes ablation member protection mechanism 445b, guides 450b, 451b, and ablation segment 435b. In is understood that any of a variety of cinching techniques can be used in conjunction with the active and return delivery electrode configurations described herein, including those cinching systems and methods described in U.S. Patent Application Nos. 60/939,201 filed May 21, 2007, Ser. No. 12/124,743 filed May 21, 2008, and Ser. No. 12/124, 766 filed May 21, 2008, the content of each of which is incorporated herein by reference.

Figure 5:
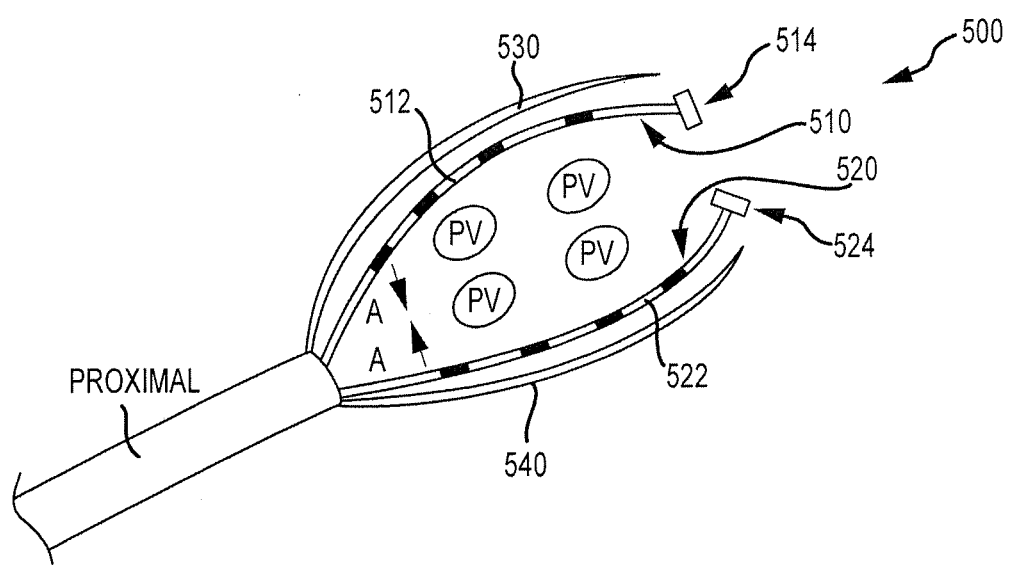
FIG. 5 illustrates aspects of tissue treatment system according to embodiments of the present invention.

As shown in FIG. 5, in some embodiments, a treatment system 500 can include a first opposing member 510 and a second opposing member 520. System 500 can also include a first electrode assembly 512 disposed on first opposing member 510 and a second electrode assembly 522 disposed on second opposing member 520. As shown here, a first coupling mechanism 514 of first opposing member 510 is configured to couple with a second coupling mechanism 524 of second opposing member 520. In some cases, distal coupling mechanisms 514, 524 may include a magnet. Treatment system 500 can also include a first compressing member 530 and a second compressing member 540. First and second compressing members 530, 540 can be semi-rigid members that operate to compress first and second opposing members 510, 520 together or toward each other, into closer proximity, as indicated by arrows A. Hence, two flexible ablation elements, each optionally coupled with an attachment mechanism to a stiffening/positioning member, could be delivered and potentially coupled at their distal end. Coupling mechanisms 514, 524 could include snap fit mechanisms, magnets, suction mechanisms, and the like. Treatment system 500 can also include active and return delivery electrode configurations as discussed elsewhere herein, for example with reference to FIGS. 1 to 3.

Figure 6:
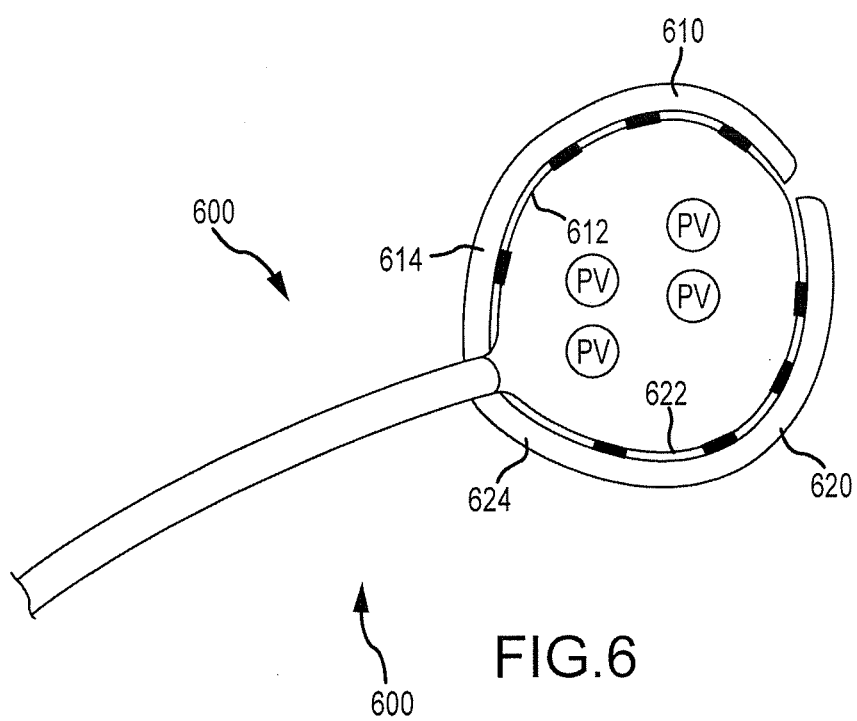
FIG. 6 illustrates aspects of tissue treatment system according to embodiments of the present invention.

As shown in FIG. 6, in some embodiments, a treatment system 600 can include a first stiffening or compressing member 610 and a second stiffening or compressing member 620. System 600 can also include a first electrode assembly 612 disposed on first stiffening or compressing member 610 and a second electrode assembly 622 disposed on second stiffening or compressing member 620. As shown here, stiffening or compressing members 610, 620 can be integrated into the ablation device or attachable and include stylets either externally attached or inserted into a channel. For example, first stiffening member 610 can include a first vacuum channel 614 and second stiffening member 620 can include a second vacuum channel 624. In some cases, stiffening or compressing member 610, 620 can include a collapsible vacuum chamber. For instance, stiffening or compressing members 610, 620 can include a thin flexible material that collapses under a vacuum. Suction applied along the length of the ablation member or electrode assembly can enhance tissue contact. As shown here, first electrode assembly 612 can include a return electrode assembly, and second electrode assembly 622 can include an active electrode assembly. Treatment system 600 can also include active and return delivery electrode configurations as discussed elsewhere herein, for example with reference to FIGS. 1 to 3.

Figure 7:
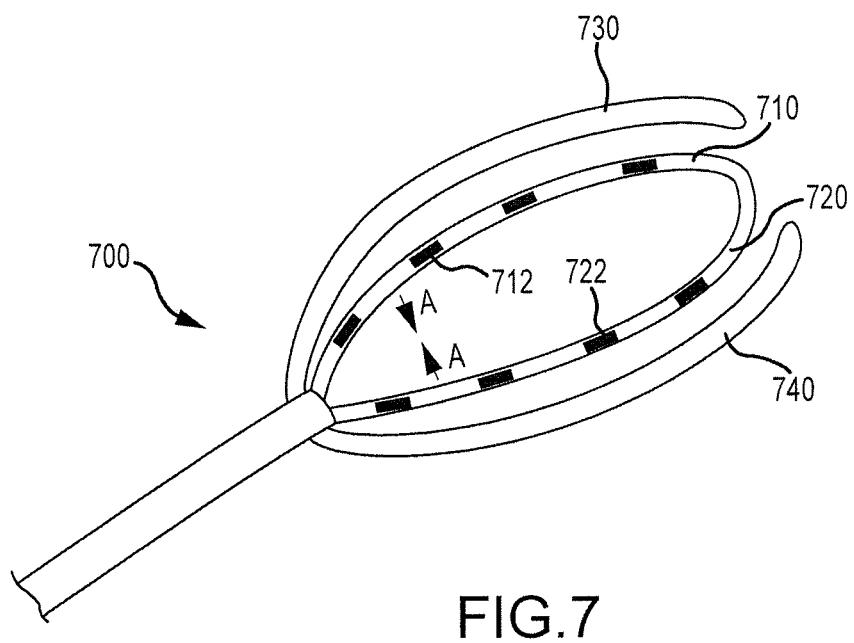
FIG. 7 illustrates aspects of tissue treatment system according to embodiments of the present invention.

As shown in FIG. 7, in some embodiments, a treatment system 700 can include a first opposing member or portion 710 and a second opposing member or portion 720. System 700 can also include a first electrode assembly 712 disposed on first opposing member 710 and a second electrode assembly 722 disposed on second opposing member 720. Treatment system 700 can also include a first compressing member 730 and a second compressing member 740. First and second compressing members 730, 740 can be balloon or expandable members that operate to compress first and second opposing members 710, 720 together or toward each other, into closer proximity, as indicated by arrows A. Treatment system 700 can also include active and return delivery electrode configurations as discussed elsewhere herein, for example with reference to FIGS. 1 to 3.

Belt devices may include visualization and delivery systems including scopes with protective lenses and introducers with stylets, sheaths, and or magnets. Relatedly, belt systems according to embodiments of the present invention may incorporate features of treatment or ablation systems such as those described in U.S. Patent Application Nos. 61/179,564 filed May 19, 2009, 61/015,472 filed Dec. 20, 2007, and Ser. No. 12/339,331 filed Dec. 19, 2008, the content of each of which is incorporated herein by reference. Belt devices can also include a marking system for identifying to the user which electrodes are or are not in contact with tissue for ablation.

According to some embodiments, the treatment systems and methods described herein may be used in conjunction or combined with aspects of introducer systems and methods such as those described in U.S. Patent Application Nos. 60/337,070 filed Dec. 4, 2001; Ser. No. 10/272,446 filed Oct. 15, 2002; Ser. No. 10/310,675 filed Dec. 4, 2002; Ser. No. 10/410,618 filed Apr. 8, 2003; Ser. No. 11/148,611 filed Jun. 8, 2005; 60/939,201 filed May 21, 2007; 61/015,472 filed Dec. 20, 2007; 61/051,975, filed May 9, 2008; Ser. No. 12/124,743 filed May 21, 2008; Ser. No. 12/124,766 filed May 21, 2008; Ser. No. 12/255,076 filed Oct. 21, 2008; Ser. No. 12/273,938 filed Nov. 19, 2008; Ser. No. 12/339,331 filed Dec. 19, 2008; Ser. No. 12/463,760 filed May 11, 2009; 61/179,564 filed May 19, 2009; 61/231,613 filed Aug. 5, 2009; and 61/241,297 filed Sep. 10, 2009. The entire content of each of these filings is incorporated herein by reference for all purposes.

Relatedly, in some instances, the treatment systems and methods described herein may include elements or aspects of the medical systems and methods discussed in U.S. Patent Application Nos. 60/337,070 filed Dec. 4, 2001; Ser. No. 10/080,374 filed Feb. 19, 2002; Ser. No. 10/255,025 filed Sep. 24, 2002; Ser. No. 10/272,446 filed Oct. 15, 2002; Ser. No. 10/310,675 filed Dec. 4, 2002; Ser. No. 10/410,618 filed Apr. 8, 2003; Ser. No. 11/067,535 filed Feb. 25, 2005; Ser. No. 11/148,611 filed Jun. 8, 2005; 60/939,201 filed May 21, 2007; 61/015,472 filed Dec. 20, 2007; 61/051,975, filed May 9, 2008; Ser. No. 12/124,743 filed May 21, 2008; Ser. No. 12/124,766 filed May 21, 2008; Ser. No. 12/255,076 filed Oct. 21, 2008; Ser. No. 12/273,938 filed Nov. 19, 2008; Ser. No. 12/339,331 filed Dec. 19, 2008; Ser. No. 12/463,760 filed May 11, 2009; 61/179,564 filed May 19, 2009; 61/231,613 filed Aug. 5, 2009; 61/241,297 filed Sep. 10, 2009; 61/288,031 filed Dec. 18, 2009; 61/318,474 filed Mar. 29, 2010; Ser. No. 12/781,072 filed May 17, 2010; and Ser. No. 12/822,616 filed Jun. 24, 2010. The entire content of each of these filings is incorporated herein by reference for all purposes.

Power Configurations

Certain known treatment systems or methods may require the application of RF ablations at least three separate times to the patient to achieve a box lesion, that is a contiguous lesion around all pulmonary veins. It is noted that a typical patient presents four pulmonary veins, but some patients have a different number of veins, the most common of those variants being five pulmonary veins. More rarely patients may have 3 or 6 pulmonary veins emptying into the left atrium. Advantageously, embodiments of the present invention can involve a reduced number of RF applications with effective results. For example, it is possible to achieve a contiguous box lesion with a reduced number of RF applications by using a device that forms a closed belt-like structure around all pulmonary veins on the left atria. In some cases, such techniques may involve two RF applications. In some cases, two applications may be helpful or required due to possible power limitations of an electrosurgical unit. For example, a reduced number of applications may require an increase in output power (e.g. double the amount of output power). Further, two applications may be helpful or required because of the very high current levels needed to power all the ablation electrodes simultaneously when using monopolar ablation to create an entire box lesion. RF ablation electrode technology may involve the application of about 3.5 to about 4.0 amperes of current to achieve and maintain the tissue temperatures needed to achieve transmural lesions for the box lesion in patients. In some cases, the maximum safe current that can be returned to the ESU through each return pad attached to the patient's skin may be about 1.0 ampere, so at least four return pads would be required. A technique involving fewer than four pads may be desirable.

According to embodiments of the present invention, it is possible to return some or all the applied current to a selected set of ablation electrodes to another set of selected ablation electrodes rather than to non-ablating electrodes so as to provide an improvement to some purely monopolar systems creating a box lesion. For example, current can be returned to selected ablation electrodes rather than to the return pads on the patient's skin. In some cases, this technique can be described as a bipolar ablation. In some cases, this approach may involve placement of the return ablation electrodes at about four or more centimeters distant from the "active" ablation electrodes. As described elsewhere herein, there are several possible or preferred patterns for active and return electrodes in which one set of electrodes is connected to an ESU power source and other electrodes return the RF current to the ESU.

It may be helpful to separately control power to all ablation electrodes, whether they are active or return electrodes, since the power requirements can vary widely at different locations on the atrium. In some instances, for the same sized electrodes, active and return electrodes can be equally effective ablation electrodes and the heating patterns produced by each can be the same. For the simplest case of one RF output and one return path to the isolated ground of the RF generator, RF power may be controlled by the average or median temperature of the selected active electrodes. Power delivery can be delivered preferentially to electrodes with the lower temperatures to maintain the electrode temperature of the selected active electrodes at nearly the same temperature. One algorithm to accomplish this is to temporarily disconnect electrodes that are hotter than the average or median temperature of the selected active electrodes by a predetermined amount (2-5° C.); an alternatively algorithm only disconnects electrodes that are hotter than the selected control temperature by a predetermined amount (2-5° C.). In the latter case all selected active electrodes can be connected to the RF power source until they individually exceed the set temperature. In a similar manner all selected return electrodes can be powered to maintain those electrodes at nearly the same temperature. As in the active electrode set, the hotter electrodes may be temporarily disconnected, for example if the electrodes exceed set temperature or if one or more exceed average or median return electrode temperatures by 2-5° C.

If the only return path for the RF current applied to the set of active ablation electrodes is through the set of return ablation electrodes, then the median or average temperatures of the active and return electrodes will often be quite different from one another even if the same size and number of electrodes are used for the active and return set. This effect can occur because ablation conditions vary by location on the heart. One method to achieve improved ablation at both active and return electrodes is to provide more ablation surface area on the active ablation sites than on the return electrode sites and return some of the RF current to return electrode pads on the skin when the return electrodes exceed a set temperature. In one algorithm, the return pads are connected to the ESU when the return ablation electrodes are disconnected. In alternative algorithm, the return pads on the patient's skin are returned to isolated ground through a path of relatively high resistance, for example 100-200 ohm, while the return ablation electrodes are connected to the isolated RF ground via a low impedance path. A higher ablation surface electrode area associated with this method can be achieved by using active ablation electrodes that have a greater surface area than the return electrodes, for example by using longer active electrodes, or using a greater number of active electrodes than return electrodes.

An alternative approach of powering all electrodes in the box lesion ablation catheter involves delivering power to all electrodes by one of two RF channels, with the second channel waveform being inverted relative to the first channel, i.e. the second channel is 180° out of phase with the first channel. The RF outputs of each channel can both source and sink RF power, for example to a maximum rating of at least 150 Watts. The connection pattern can include the patterns as illustrated elsewhere herein. In some cases, the electrodes shown as being returned to the isolated ground of the RF power generator can instead be connected to the second RF channel. For each RF output, RF power can be controlled by the average or median temperature of the selected active electrodes connected to that output channel. Power delivery can be delivered preferentially to electrodes with the lower temperatures to maintain the electrode temperature of the selected active electrodes at nearly the same temperature. One algorithm to accomplish this is to temporarily disconnect electrodes that are hotter than the average or median temperature of the selected active electrodes by a predetermined amount (2-5° C.); alternatively an algorithm can be used that only disconnects electrodes that are hotter than the selected control temperature by a predetermined amount (2-5° C.). In the latter case all selected active electrodes can be connected to the RF power source until they individually exceeded the set temperature. As with the bipolar situation with a single output channel, temperatures of the ablation electrodes connected to the two output channels may not be the same if return pads on the patients skin are not used, since currents sourced from one channel are typically sunk in the other channel. In other words, according to such embodiments, with no return pads, the total current from all electrodes connected to channel 1 is equal to the total current through electrodes connected to channel 2. With return pads connected to the isolated ground of the channel outputs, the current amplitudes on channel 1 and channel 2 can differ. The difference in current levels flowing through channels 1 and 2 flows to the return pads and is returned to the RF generator. Usually the current required to ablate tissues at the electrodes connected to channel 1 is similar to the current required to ablate tissue in the electrodes connected to channel 2. Therefore, the difference in the current amplitudes provided by channels 1 and 2 is much smaller than the currents in each channel and is smaller than the sum of the currents flowing in each channel, which is the current amplitude that is ablating tissue in the box lesion. For these reasons, the current flowing through the return pads is usually manifold lower than currents that are flowing through all the selected ablation electrodes (or the sum of the current amplitudes provided by channels 1 and 2). In some cases, systems and methods involve the use of equivalent RF frequencies or phases applied to different electrodes.

With three or more separate RF output channels, separate power control to the differing ablation electrodes can be achieved without use of grounding pads on the patient's skin. If a single RF frequency is used, then signals with 120° phase angle differences among the three channels can be used, and other phase choices can provide acceptable performance as well. If no return pad is used, it may be helpful if phase angles for three output channels using the same frequency differ by more than 30°. If more than one electrode is connected to a single output, then the methods previously described to maintain those electrodes at similar temperatures can be used. If four or more output channels are used, then equal phase separation among the output channels may be used, i.e. 360°/N where N is the number of output channels used.

The frequencies used for the output channels need not be at the same. Use of differing frequencies can have advantages, for example if three or more output channels are used, and the output waveforms from each channel are uncorrelated to each other. For such waveforms, changes in one channel has no impact on the other channels, which simplifies power control for the entire system.

According to some ablation system embodiments, co-axial electrode separation can be about 2 mm to enable regional control of the ablation process while preventing gaps in the ablation pattern between electrodes. Such spacing can be optimized based on the methods of activating those electrodes: the electrodes can be actively maintained at the same potentials during ablation, or they can be disconnected from the RF generator. For activation patterns that have co-axial electrodes actively maintained at different potentials, electrode distances can be increased to 4-8 mm to prevent char formation between electrodes. Since current densities are high in the tissue between closely spaced electrodes for bipolar or other activation schemes described in this disclosure, when those co-axial electrodes are selected for ablation, the region between the electrodes are overheated, resulting in char formation between the electrodes. On the other hand, if the co-axial electrodes are never activated simultaneously, or if the same potentials are applied to each adjacent co-axial electrode, then a gap may occur between the electrodes separated by 4-8 mm. In some instances, systems and methods may not involve the use of different RF frequencies or phases applied to different electrodes.

It is appreciated that system embodiments of the present in invention can be configured to carry out any of the various method aspects disclosed herein. Likewise, embodiments of the present invention encompass methods which are performed by any of the systems described herein.

While the exemplary embodiments have been described in some detail, by way of example and for clarity of understanding, those of skill in the art will recognize that a variety of modification, adaptations, and changes may be employed. Hence, the scope of the present invention should be limited solely by the claims.

What is claimed is:

1. A radiofrequency ablation system for treating a tissue of a patient, comprising:
    an ablation apparatus having a first electrode assembly carried by a flexible tube structure and a second electrode assembly carried by the flexible tube structure, wherein the first electrode assembly comprises a plurality of electrodes present as a continuous set of alternating delivery and return electrodes disposed along a first length of the flexible tube structure, the plurality of electrodes of the first electrode assembly comprising a first delivery electrode and a first return electrode disposed distal to the first delivery electrode, and the second electrode assembly comprises a plurality of electrodes present as a continuous set of alternating delivery and return electrodes disposed along a second length of the flexible tube structure, the plurality of electrodes of the second electrode assembly comprising a second delivery electrode and a second return electrode disposed distal to the second delivery electrode, wherein the second electrode assembly is disposed distal to the first electrode assembly along the flexible tube structure, wherein the first length of the flexible tube structure and the second length of the flexible tube structure do not overlap along the flexible tube structure, wherein the first delivery electrode of the first electrode assembly is configured to pair with the second return electrode of the second electrode assembly for producing bipolar ablation, wherein the second delivery electrode of the second electrode assembly is configured to pair with the first return electrode of the first electrode assembly for producing bipolar ablation, and wherein an ablation surface area of the first delivery electrode is greater than an ablation surface area of the second return electrode and an ablation surface area of the second delivery electrode is greater than an ablation surface area of the first return electrode;
    a radiofrequency generator configured to deliver a respective radiofrequency power signal to each of the delivery electrodes of the first electrode assembly and the second electrode assembly of the ablation apparatus and to return each respective power signal from the corresponding paired return electrodes of the first electrode assembly and the second electrode assembly;
    a plurality of wires comprising a respective wire corresponding to each delivery electrode of the first electrode assembly and the second electrode assembly, wherein each respective wire is configured to transmit the respective radiofrequency power signal from the radiofrequency generator to the respective delivery electrode of the first electrode assembly and the second electrode assembly; and
    a control mechanism configured to enable temperature-based power control to each of the delivery electrodes of the first electrode assembly and the second electrode assembly.

2. The radiofrequency ablation system as in claim 1, wherein each respective power signal is delivered by an output of the radiofrequency generator and is returned by a return path of the radiofrequency generator.

3. The radiofrequency ablation system as in claim 2, wherein the ablation apparatus is adapted to enable placement of the first delivery electrode and the first return electrode of the first electrode assembly and the second delivery electrode and the second return electrode of the second electrode assembly near one or more pulmonary veins of the patient.

4. The radiofrequency ablation system as in claim 2, wherein the ablation apparatus is adapted to enable ablation of atrial tissue at least partially encircling one or more pulmonary veins of the patient.

5. The radiofrequency ablation system as in claim 2, wherein the ablation apparatus is adapted to enable ablation of atrial tissue to isolate tissue activation within at least one pulmonary vein from a portion of the atrium.

6. The radiofrequency ablation system as in claim 2, wherein the ablation apparatus is adapted to provide a contiguous lesion around all pulmonary veins without needing to move the delivery and return electrodes during a lesion-making process.

7. The radiofrequency ablation system as in claim 2, wherein the ablation apparatus is configured to form a loop.

8. The radiofrequency ablation system as in claim 7, further comprising a cinching structure configured to form the loop.

9. The radiofrequency ablation system as in claim 8, wherein the cinching structure comprises magnets configured to form the loop.

10. The radiofrequency ablation system as in claim 8, wherein the cinching structure comprises a snap connection that provides an interference fit configured to form the loop.

11. The radiofrequency ablation system as in claim 8, wherein the cinching structure is configured to provide suction that forms the loop.

12. The radiofrequency ablation system as in claim 1, wherein a first one of the respective radiofrequency power signals is delivered by a first output of the radiofrequency generator and a second one of the respective radiofrequency power signals is delivered by a second output of the radiofrequency generator.

13. The radiofrequency ablation system as in claim 12, wherein the radiofrequency generator is configured to generate the first one of the respective radiofrequency power signals delivered by the first output and the second one of the respective radiofrequency power signals delivered by the second output such that the first one of the respective radiofrequency power signals and the second one of the respective radiofrequency power signals have the same frequency but differ in amplitude, phase, or both.

14. The radiofrequency ablation system as in claim 13, wherein one or more electrode pads placed on the skin of the patient provide a return path to the radiofrequency generator.

15. The radiofrequency ablation system as in claim 12, wherein the radiofrequency generator is configured to generate the first one of the respective radiofrequency power signals delivered by the first output and the second one of the respective radiofrequency power signals delivered by the second output such that the first one of the respective radiofrequency power signals and the second one of the respective radiofrequency power signals have different frequencies.

16. The radiofrequency ablation system as in claim 15, wherein one or more electrode pads placed on the skin of the patient provide a return path to the radiofrequency generator.

17. The radiofrequency ablation system as in claim 1, wherein one or more electrode pads placed on the skin of the patient provide a return path to the radiofrequency generator.

18. The radiofrequency ablation system as in claim 1, wherein the ablation apparatus is adapted to enable placement of the first delivery electrode and the first return electrode of the first electrode assembly and the second delivery electrode and the second return electrode of the second electrode assembly on an epicardium of a heart of the patient.

19. The radiofrequency ablation system as in claim 1, wherein the ablation apparatus is adapted to provide a contiguous lesion around all pulmonary veins without needing to move the first delivery electrode and the first return electrode of the first electrode assembly and the second delivery electrode and the second return electrode of the second electrode assembly during a lesion-making process.

20. The radiofrequency ablation system as in claim 1, wherein the ablation apparatus includes one or more suction pods configured to enhance tissue contact to the delivery and return electrodes.

21. A method of administering a radiofrequency ablation treatment to a patient, comprising:
contacting the patient with an ablation apparatus having a first electrode assembly carried by a flexible tube structure and a second electrode assembly carried by the flexible structure, wherein the first electrode assembly comprises a plurality of electrodes present as a continuous set of alternating delivery and return electrodes disposed along a first length of the flexible structure, the plurality of electrodes of the first electrode assembly comprising a first delivery electrode and a first return electrode disposed distal to the first delivery electrode, and the second electrode assembly comprises a plurality of electrodes present as a continuous set of alternating delivery and return electrodes disposed along a second length of the flexible structure, the plurality of electrodes of the second electrode assembly comprising a second delivery electrode and a second return electrode disposed distal to the second delivery electrode, wherein the second electrode assembly is disposed distal to the first electrode assembly along the flexible tube structure, wherein the first length of the flexible structure and the second length of the flexible structure do not overlap along the flexible structure, wherein the first delivery electrode of the first electrode assembly is configured to pair with the second return electrode of the second electrode assembly for producing bipolar ablation, wherein the second delivery electrode of the second electrode assembly is configured to pair with the first return electrode of the first electrode assembly for producing bipolar ablation, and wherein an ablation surface area of the first delivery electrode is greater than an ablation surface area of the second return electrode and an ablation surface area of the second delivery electrode is greater than an ablation surface area of the first return electrode;
delivering a respective radiofrequency power signal to each of the delivery electrodes of the first electrode assembly and the second electrode assembly of the ablation apparatus and returning each respective power signal from the corresponding paired return electrodes of the first electrode assembly and the second electrode assembly;
sensing a temperature of a tissue of the patient; and
controlling a power to one or more of the delivery electrodes of the first electrode assembly and the second electrode assembly based on the sensed temperature.

22. The method as in claim 21, further comprising using an introducer during the contacting step.

23. The method as in claim 21, further comprising using an endoscopic visualization apparatus during the contacting step.

24. A radiofrequency ablation system for treating a tissue comprising:
an ablation apparatus having a first electrode assembly carried by a flexible tube structure and a second electrode assembly carried by the flexible tube structure, wherein the first electrode assembly comprises a plurality of electrodes present as a continuous set of alternating delivery and return electrodes disposed along a first length of the flexible tube structure, the plurality of electrodes of the first electrode assembly comprising a first delivery electrode and a first return electrode disposed distal to the first delivery electrode, and the second electrode assembly comprises a plurality of electrodes present as a continuous set of alternating delivery and return electrodes disposed along a second length of the flexible tube structure, the plurality of electrodes of the second electrode assembly comprising a second delivery electrode and a second return electrode disposed distal to the second delivery electrode, wherein the second electrode assembly is disposed distal to the first electrode assembly along the flexible tube structure, wherein the first length of the flexible tube structure and the second length of the flexible tube structure do not overlap along the flexible tube structure,
wherein the first delivery electrode of the first electrode assembly is configured to pair with the second return electrode of the second electrode assembly for producing bipolar ablation, wherein the second delivery electrode of the second electrode assembly is configured to pair with the first return electrode of the first electrode assembly for producing bipolar ablation, and wherein an ablation surface area of the first delivery electrode is greater than an ablation surface area of the second return electrode and an ablation surface area of the second delivery electrode is greater than an ablation surface area of the first return electrode;
a radiofrequency generator configured to generate a first radiofrequency power signal for the first electrode assembly and a second radiofrequency power signal for the second electrode assembly;
a first transmission element configured to transmit the first radiofrequency power signal from the radiofrequency generator to the first electrode assembly and a second transmission element configured to transmit the second radiofrequency power signal from the radiofrequency generator to the second electrode assembly; and
a control mechanism configured to enable temperature-based power control to the first electrode assembly and the second electrode assembly.

25. The radiofrequency ablation system as in claim 24, wherein the first radiofrequency power signal is equivalent to the second radiofrequency power signal.

26. The radiofrequency ablation system as in claim 24, wherein the first radiofrequency power signal is different from the second radiofrequency power signal.

27. A method of administering a radiofrequency ablation treatment to a patient, comprising:

contacting the patient with an ablation apparatus having a first electrode assembly and a second electrode assembly, wherein the first electrode assembly comprises a plurality of electrodes present as a continuous set of alternating delivery and return electrodes disposed along a first length of a flexible structure, the plurality of electrodes of the first electrode assembly comprising a first delivery electrode and a first return electrode disposed distal to the first delivery electrode, and the second electrode assembly comprises a plurality of electrodes present as a continuous set of alternating delivery and return electrodes disposed along a second length of the flexible structure, the plurality of electrodes of the second electrode assembly comprising a second delivery electrode and a second return electrode disposed distal to the second delivery electrode, wherein the second electrode assembly is disposed distal to the first electrode assembly along the flexible tube structure, wherein the first length of the flexible structure and the second length of the flexible structure do not overlap along the flexible structure, wherein the first delivery electrode of the first electrode assembly is configured to pair with the second return electrode of the second electrode assembly for producing bipolar ablation, wherein the second delivery electrode of the second electrode assembly is configured to pair with the first return electrode of the first electrode assembly for producing bipolar ablation, and wherein an ablation surface area of the first delivery electrode is greater than an ablation surface area of the second return electrode and an ablation surface area of the second delivery electrode is greater than an ablation surface area of the first return electrode;

delivering a first radiofrequency power signal to the first electrode assembly of the ablation apparatus;

delivering a second radiofrequency power signal to the second electrode assembly of the ablation apparatus;

sensing a temperature of a tissue of the patient; and controlling a power to at least one of the first electrode assembly or the second electrode assembly based on the sensed temperature.

28. The method as in claim 27, wherein the first radiofrequency power signal is equivalent to the second radiofrequency power signal.

29. The method as in claim 27, wherein the first radiofrequency power signal is different from the second radiofrequency power signal.

30. A radiofrequency ablation system for treating a tissue of a patient, comprising:

an ablation apparatus having a first electrode assembly carried by a flexible tube structure and a second electrode assembly carried by the flexible tube structure, wherein the first electrode assembly comprises two electrodes present as a continuous set of alternating delivery and return electrodes disposed along a first length of the flexible tube structure, such that the first electrode assembly comprises a first delivery electrode and a first return electrode disposed distal to the first delivery electrode, wherein the second electrode assembly comprises two electrodes present as a continuous set of alternating delivery and return electrodes disposed along a second length of the flexible tube structure, such that the second electrode assembly comprises a second delivery electrode and a second return electrode disposed distal to the second delivery electrode, wherein the second electrode assembly is disposed distal to the first electrode assembly along the flexible tube structure, wherein the first length of the flexible tube structure and the second length of the flexible tube structure do not overlap along the flexible tube structure, wherein the first delivery electrode of the first electrode assembly is configured to pair with the second return electrode of the second electrode assembly for producing bipolar ablation, wherein the second delivery electrode of the second electrode assembly is configured to pair with the first return electrode of the first electrode assembly for producing bipolar ablation, and wherein an ablation surface area of the first delivery electrode is greater than an ablation surface area of the second return electrode and an ablation surface area of the second delivery electrode is greater than an ablation surface area of the first return electrode;

a radiofrequency generator configured to deliver a respective radiofrequency power signal to each of the delivery electrodes of the first electrode assembly and the second electrode assembly of the ablation apparatus and to return each respective power signal from the corresponding paired return electrodes of the first electrode assembly and the second electrode assembly;

a plurality of wires comprising a respective wire corresponding to each delivery electrode of the first electrode assembly and the second electrode assembly, wherein each respective wire is configured to transmit the respective radiofrequency power signal from the radiofrequency generator to the respective delivery electrode of the first electrode assembly and the second electrode assembly;

an electrode pad that provides a return path to the radiofrequency generator; and a control mechanism configured to enable temperature-based power control to each of the delivery electrodes of the first electrode assembly and the second electrode assembly, wherein the control mechanism is configured to return radiofrequency current to the electrode pad when the first return electrode and the second return electrode exceed a set temperature.

31. The radiofrequency ablation system as in claim 30, wherein the return path provided by the electrode pad has a resistance between 100 ohm and 200 ohm.

* * * * *